(12) United States Patent
Koomen et al.

(10) Patent No.: US 9,410,967 B2
(45) Date of Patent: Aug. 9, 2016

(54) METHODS AND MATERIALS FOR MONITORING MYELOMA USING QUANTITATIVE MASS SPECTROMETRY

(71) Applicant: H. Lee Moffitt Cancer Center and Research Institute, Inc., Tampa, FL (US)

(72) Inventors: John Matthew Koomen, Tampa, FL (US); Elizabeth Renee Remily, Lutz, FL (US); Kaaron Benson, Apollo Beach, FL (US); Mohamad Hussein, Odessa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 13/905,549

(22) Filed: May 30, 2013

(65) Prior Publication Data

US 2013/0260406 A1      Oct. 3, 2013

Related U.S. Application Data

(62) Division of application No. 12/997,210, filed as application No. PCT/US2009/049286 on Jun. 30, 2009, now abandoned.

(60) Provisional application No. 61/076,907, filed on Jun. 30, 2008.

(51) Int. Cl.
*G01N 33/68* (2006.01)
*C07K 16/06* (2006.01)

(52) U.S. Cl.
CPC .......... *G01N 33/6857* (2013.01); *C07K 16/065* (2013.01)

(58) Field of Classification Search
CPC ............. C07K 16/065; G01N 33/6857; G01N 33/5088; G01N 33/6854; G01N 2033/00; G01N 2033/483; G01N 2033/50; G01N 2800/00; G01N 2800/60; G01N 2800/52; G01N 2800/50; G01N 2800/24
See application file for complete search history.

(56) References Cited

U.S. PATENT DOCUMENTS

| | | | |
|---|---|---|---|
| 7,163,803 B2 | 1/2007 | Hamon et al. | |
| 7,544,518 B2 | 6/2009 | Aebersold et al. | |
| 2004/0203023 A1 | 10/2004 | Chandrasiri Herath | 435/6 |
| 2009/0011447 A1 | 1/2009 | Banoub et al. | |
| 2009/0148951 A1 | 6/2009 | Zhang et al. | |

OTHER PUBLICATIONS

According to Medline Plus (http://www.nlm.nih.gov/medlineplus/ency/article/000816.htm, updated May 29, 2011).*
Labs tests online (http://labtestsonline.org/understanding/conditions/mult-myeloma/start/2-copyright 2001-2014).*
Tassone et al. (European Journal of Cancer, 42 (2006) 1530-1538).*
Anderson, L and Hunter, CL, "Quantitative mass spectrometric multiple reaction monitoring assays for major plasma proteins," *Molecular & Cellular Proteomics*, 2006, 6:573-588.
Chanan-Khan, AA and Lee, K, "Pegylated liposomal doxorubicin and immunomodulatory drug combinations in multiple myeloma: rationale and clinical experience," *Clinical Lymphoma & Myeloma*, 2007, 7(Suppl 4):S163-S169.
Chauhan, D et al., "Interleukin-6 inhibits Fas-induced apoptosis and stress-activated protein kinase activation in multiple myeloma cells," *Blood*, 1997, 89:227-234.
Chen, Q et al., "The FA/BRCA pathway is involved in Melphalan-induced DNA interstrand cross-link repair and accounts for Melphalan resistance in multiple myeloma cells," *Blood*, 2005, 106:698-705.
Dalton, WS, "The tumor microenvironment: focus on myeloma," *Cancer Treatment Reviews*, 2003, 29(Suppl 1):11-19.
Damiano, JS et al., "Cell adhesion mediated drug resistance (CAM-DR): role of integrins and resistance to apoptosis in human myeloma cell lines," *Blood*, 1999, 93:1658-1667.
Deutsch, EW et al., "Peptide Atlas: a resource for target selection for emerging targeted proteomics workflows," *EMBO Reports*, May 2008, 9(5): 429-434.
Durie, BGM and Salmon, SE, "A clinical staging system for multiple myeloma. Correlation of measured myeloma cell mass with presenting clinical features, response to treatment, and survival," *Cancer*, 1975, 36:842-854.
Falco, P et al., "Melphalan and its role in the management of patients with multiple myeloma," *Expert Rev. Anticancer Ther.*, 2007, 7(7):945-957.
Fonseca, R and Stewart, AK, "Targeted therapeutics for multiple myeloma: the arrival of a risk-stratified approach," *Mol. Cancer Ther.*, Mar. 2007, 6(3):802-810.
Greipp, PR et al., "International staging system for multiple myeloma," *Journal of Clinical Oncology*, May 20, 2005, 23(15):3412-3420.

(Continued)

*Primary Examiner* — James H Alstrum Acevedo
*Assistant Examiner* — Tara Martinez
(74) *Attorney, Agent, or Firm* — Meunier Carlin & Curfman LLC (57) ABSTRACT

The subject invention concerns methods and materials for diagnosing, monitoring the progress, and/or providing a prognosis for multiple myeloma and other conditions associated with antibody production in a person or animal. The methods of the invention utilize mass spectrometry for quantitative monitoring and detection of antibody produced by the plasma cells. The methods of the invention can be utilized for diagnosis, monitoring, and/or prognosis of multiple myeloma, monoclonal gammopathy, and other immunological or hematological conditions and disorders. In addition to detecting and quantifying antibody in a sample, other biological markers, such as serum albumin and/or beta-2-microglobulin, can also be detected and quantified using the present invention, and in combination with detection and quantification of antibody. Thus, in one embodiment, both antibody and serum albumin and/or beta-2-microglobulin are detected and quantified using mass spectrometry and a diagnosis or prognosis made based on the results and levels detected.

17 Claims, 3 Drawing Sheets

(56) References Cited

OTHER PUBLICATIONS

Hazlehurst, LA et al., "Role of the tumor microenvironment in mediating de novo resistance to drugs and physiological mediators of cell death," *Oncogene*, 2003, 22:7396-7402.
Kirkpatrick, DS et al., "The abtolute quantification strategy: a general procedure for the quantification of proteins and post-translational modifications," *Methods*, Jan. 2005, 35(3): 265-273.
Koomen, JM et al., "Proteomic contributions to personalized cancer care," *Molecular and Cellular Proteomics*, Jul. 2008, 7(10): 1780-1794.
Kuhn, E et al., "Quantification of C-reactive protein in the serum of patients with rheumatoid arthritis using multiple reaction monitoring mass spectrometry and $^{13}$C-labeled peptide standards," *Proteomics*, 2004, 4:1175-1186.
Kyle, RA et al., "Prevalence of monoclonal gammopathy of undetermined significance," *The New England Journal of Medicine*, 2006, 354:1362-1369.
Lange, V et al., "Targeted quantitative analysis of *Streptococcus pyogenes* virulence factors by multiple reaction monitoring," *Molecular and Cellular Proteomics*, Apr. 2008, 7(8): 1489-1500.
Li, Z-W and Dalton, WS, "Tumor microenvironment and drug resistance in hematologic malignancies," *Blood Reviews*, 2006, 20(6):333-342.
Lüftner, D et al., "Clinical value of bisphosphonates in cancer therapy," *Anticancer Research*, 2007, 27:1759-1768.
Ma, MH et al., "The proteasome Inhibitor PS-341 markedly enhances sensitivity of multiple myeloma tumor cells to chemotherapeutic agents," *Clinical Cancer Research*, 2003, 9;1136-1144.
Mallick, P et al., "Computational prediction of proteotypic peptides for quantitative proteomics," *Nature Biotechnology*, Dec. 2006, 25(1): 125-131.
Manochakian, R et al., "Clinical Impact of Bortezomib in frontline regimens for patients with multiple myeloma," *The Oncologist*, 2007, 12:978-990.
Meister, S et al. "Extensive immunoglobulin production sensitizes myeloma cells for proteasome inhibition," *Cancer Research*, 2007, 67:1783-1792.
Merchionne, F et al., "New therapies in multiple myeloma," *Clin. Exp. Med.*, 2007, 7:83-97.
Podar, K et al., "Up-regulation of c-Jun inhibits proliferation and induces apoptosis via caspase-triggered c-Abl cleavage in human multiple myeloma," *Cancer Res.* 2007, 67(4):1680-1688.
Richardson, PG. et al., "The emerging role of novel therapies for the treatment of relapsed myeloma," *Journal of the National. Comprehensive Cancer Network*, Feb. 2007, 5(2):149-162.
Singhal, S and Mehta, J, "Lenalidomide in myeloma," *Current Treatment Options in Oncology*, 2007, 8:154-163.
Srikanth, M et al., "An update on drug combinations for treatment of myeloma," *Expert Opin. Investig. Drugs*, 2008, 17(1):1-12.
Thomas, S and Alexanian, R, "Current treatment strategies for multiple myeloma," *Clinical Lymphoma & Myeloma*, 2007, 7(Suppl 4):S139-S144.
Urashima, M et al., "Interleukin-6 overcomes p21WAF1 upregulation and G1 growth arrest induced by dexamethasone and interferon-γ in multiple myeloma cells," *Blood*, 1997, 90:279-289.
Voorhees, PM and Orlowski, RZ, "Emerging data on the use of anthracyclines in combination with Bortezomib in multiple myeloma," *Clinical Lymphoma & Myeloma*, 2007, 7(Suppl 4):S156-S162.
Kirkpatrick et al. (The absolute quantification strategy: a general procedure for the quantification of proteins and post-Kirkpatrick et al. The absolute quantification strategy: a general procedure for the quantification of proteins and post-translational modification, Methods vol. 35 (2005) pp. 265-273.
Ramachandran et al. (Identification of N-Linked Glycoproteins in Human Saliva by A8 Glycoprotein Capture and Mass Spectrometry, The Journal of Proteome Research 2006, 5, pp. 1493-1503.
Kirkpatrick DS et al. "The absolute quantification strategy: a general procedure for the quantification of proteins and post-translational modifications." Methods. Mar. 2005;35(3):265-73.
Ramachandran P, et al. "Identification of N-linked glycoproteins in human saliva by glycoprotein capture and mass spectrometry." J Proteome Res. Jun. 2006;5(6):1493-503.
Kuhn E, et al. "Quantification of C-reactive protein in the serum of patients with rheumatoid arthritis using multiple reaction monitoring mass spectrometry and 13C-labeled peptide standards." Proteomics. Apr. 2004;4(4):1175-86.

\* cited by examiner

METHODS AND MATERIALS FOR MONITORING MYELOMA USING QUANTITATIVE MASS SPECTROMETRY

CROSS-REFERENCE TO RELATED APPLICATION

The application is a divisional application of U.S. application Ser. No. 12/997,210, filed Mar. 3, 2011, which is a 371 national phase of PCT/US09/049286, filed on Jun. 30, 2009, and which claims priority to U.S. Provisional Application No. 61/076,907, filed Jun. 30, 2008, all of which are incorporated herein by reference in their entirety.

BACKGROUND OF THE INVENTION

Multiple myeloma (MM) is a cancer of the plasma cell, which primarily develops in the elderly population. The progression of the tumor is well understood, and it can be diagnosed by the presence of multiple myeloma cells in the bone marrow and monitored by the amount of antibody secretion from the clonal population of plasma cells. A premalignant condition known as monoclonal gammopathy of undetermined significance (MGUS) develops at certain rates in the U.S. population: 3% at age 50, 5% at age 70, and 7% by age 85; approximately 1% of MGUS patients progress to multiple myeloma on an annual basis (Kyle et al., 2006). The molecular causes for progression from MGUS to MM are unknown. After the onset of the cancer, multiple myeloma patients suffer from several symptoms, including calcium dysregulation, renal failure, anemia, and bone lesions. A diagnosis of multiple myeloma is established using blood and urine tests. For advanced stage patients, complete skeletal surveys are also used to examine the damage caused by multiple myeloma in the bone marrow. Staging with serum calcium, creatinine, hemoglobin, and most importantly, the concentration of the "monoclonal serum protein" was established in 1975 by Durie and Salmon (Durie and Salmon, 1975). The International Staging System determined in 2005 uses those markers as well as serum albumin and β-2-microglobulin (Greipp et al., 2005). The survival statistics indicate the importance of early detection and proper staging, and show the devastating impact of multiple myeloma. Stage I patients have median survival times of 62 months, stage II 45 months, and stage III patient median survival is reduced to 29 months.

Despite the highly specific and easily detectable biomarkers, many challenges still exist for MM treatment. Several different treatment regimens are under investigation: these strategies have been the subject of numerous recent reviews (Fonseca and Stewart, 2007; Chanan-Khan and Lee, 2007; Thomas and Alexanian, 2007; Falco et al., 2007). Novel therapeutic strategies include proteasome inhibition with agents like bortezomib (Voorhees and Orlowski, 2007; Manochakian et al., 2007) and a combination of cancer cell targeting and immune modulation with thalidomide derivatives like Lenalidomide (Singhal and Mehta, 2007). While each of these agents can have some success against multiple myeloma cells, proteasome inhibitors are the only molecularly guided therapy to date: treatment is more effective for patients with myelomas that secrete high levels of monoclonal antibodies (Meister et al., 2007). The use of the other agents is directed by the expected tolerance for side effects rather than molecular targeting. Regardless, these agents improve the patient outcome when compared to the current standard of care (Ma et al., 2003), and drug combination strategies are currently in clinical trials (Srikanth et al., 2008; Richardson et al., 2007; Merchionne et al., 2007). Proteomic research may contribute to guidance of existing and emerging therapies. Identification of novel targets including c-Jun and the Fanconi anemia pathway (Chen et al., 2005) also offers opportunities to examine protein expression, binding partners, and post-translational modification. Furthermore, the bone marrow microenvironment is critical for progression of multiple myeloma and likely contributes to drug resistance; (Li and Dalton, 2006; Harlehurst et al., 2003; Dalton, 2003) this knowledge has led to preclinical models examining multiple myeloma in the context of the bone marrow microenvironment. Plausible targets in the bone marrow microenvironment include cytokine signaling, e.g. IL-6, (Chauhan et al., 1997; Urashima et al., 1997) and integrin mediated drug resistance (Damiano et al., 1999). Proteome analysis may make a significant contribution here as well.

Patient monitoring strategies present significant challenges, particularly in the detection of MGUS patients most likely to develop multiple myeloma and ongoing assessment of relapse or recurrence in previously treated multiple myeloma patients. Many MM patients who have undergone treatment are repetitively checked at two week or four week intervals, leading to high numbers of clinic visits and collection of large volumes of blood. Methods for patient sampling and detection of the monoclonal serum protein are presented from a process chemistry standpoint. Process chemists use extensive background knowledge of synthesis, analysis, and engineering to redesign industrial assembly lines or improve individual steps in manufacturing.

BRIEF SUMMARY OF THE INVENTION

The subject invention concerns methods and materials for diagnosing, monitoring the progress, and/or providing a prognosis for multiple myeloma and other conditions associated with antibody production in a person or animal. In one embodiment, quantitative mass spectrometry is used to monitor the amount of multiple myeloma cells in patients using serum samples. Each MM tumor secretes a specific (monoclonal) antibody; the amount of the tumor in the blood or bone marrow of a patient can be measured by the detection of this protein. Current methods use gel or capillary electrophoresis to monitor the relative amount and identify the type of the antibody that is secreted by the MM cells. The quantitative mass spectrometry techniques of the present invention combines these two measurements and can provide for absolute quantification for each of the antibody chains (A, D, E, G, and M, as well as kappa and lambda) in MM patients. Proteolytic peptides are used as surrogate biomarkers to measure the amount of the monoclonal antibody expressed in patients' sera. The methods of the present invention can be applied to MM patients, patients with the premalignant condition, monoclonal gammopathy of undetermined significance (MGUS), and other immune or blood disorders, such as Waldenstrom's macroglobulinemia or HIV/AIDS. Additional diagnostic markers, including but not limited to serum albumin and beta-2-microglobulin, can also be quantified using the present invention.

In one embodiment of a method of the invention, monoclonal antibody proteins were excised from serum protein electrophoresis gels and digested with trypsin. Following trypsin digestion, the resulting isolated proteolytic peptides were sequenced with liquid chromatography coupled to tandem mass spectrometry. Using the results from several patient samples, specific peptides were selected to monitor each type of antibody (A, D, E, G, and M), as well as kappa and lambda light chain and other diagnostic molecules like serum albumin and beta-2-microglobulin (see Table 1). After selecting peptides that were consistently detected in all patient samples, a quantitative assay was developed using liquid chromatography coupled to multiple reaction monitoring (LC-MRM) on a triple quadrupole mass spectrometer. After overnight digestion of patient serum, the peptides are analyzed in a 45-minute experiment separating them by reverse phase and filtering them by molecular weight and sequence specific fragment ions. Using these transitions (pairs of intact molecules and fragments), individual peptide molecules can be selectively quantified, even from a complex matrix like human blood serum. The methods of the present invention have been proven effective with control serum and patient samples. Absolute quantification is obtained by spiking in known amounts of synthetic peptide containing heavy isotope labels, e.g. $^{13}$C and $^{15}$N or by creating a mass shift by substituting an amino acid with one of a similar composition (such as Alanine for Glycine).

BRIEF DESCRIPTION OF THE SEQUENCES

SEQ ID NO:1 is a peptide sequence of the invention (IGHA1, 2).
SEQ ID NO:2 is a peptide sequence of the invention (IGHA1, 2).
SEQ ID NO:3 is a peptide sequence of the invention (IGLHA1).
SEQ ID NO:4 is a peptide sequence of the invention (IGHG1, 3).
SEQ ID NO:5 is a peptide sequence of the invention (IGHG1, 2).
SEQ ID NO:6 is a peptide sequence of the invention (IGHG1, 2).
SEQ ID NO:7 is a peptide sequence of the invention (IGHG1).
SEQ ID NO:8 is a peptide sequence of the invention (IGHG2).
SEQ ID NO:9 is a peptide sequence of the invention (IGHG3).
SEQ ID NO:10 is a peptide sequence of the invention (IGHG3, 4).
SEQ ID NO: 11 is a peptide sequence of the invention (IGHG4).
SEQ ID NO:12 is a peptide sequence of the invention (IGHM).
SEQ ID NO: 13 is a peptide sequence of the invention (IGHM).
SEQ ID NO: 14 is a peptide sequence of the invention (IGHM).
SEQ ID NO:15 is a peptide sequence of the invention (IGKC).
SEQ ID NO:16 is a peptide sequence of the invention (IGKC).
SEQ ID NO:17 is a peptide sequence of the invention (IGKC).
SEQ ID NO: 18 is a peptide sequence of the invention (LAC).
SEQ ID NO: 19 is a peptide sequence of the invention (LAC).
SEQ ID NO:20 is a peptide sequence of the invention (IGHE).
SEQ ID NO:21 is a peptide sequence of the invention (IGHE).
SEQ ID NO:22 is a peptide sequence of the invention (IGHD).
SEQ ID NO:23 is a peptide sequence of the invention (IGHD).
SEQ ID NO:24 is a peptide sequence of the invention (IGHD).
SEQ ID NO:25 is a peptide sequence of the invention (ALBU).
SEQ ID NO:26 is a peptide sequence of the invention (ALBU).
SEQ ID NO:27 is a peptide sequence of the invention (ALBU).
SEQ ID NO:28 is a peptide sequence of the invention.
SEQ ID NO:29 is a peptide sequence of the invention.
SEQ ID NO:30 is a peptide sequence of the invention.

DETAILED DESCRIPTION OF THE INVENTION

The subject invention concerns methods and materials for diagnosing, monitoring the progress, and/or providing a prognosis for multiple myeloma and other diseases or conditions associated with antibody production in a person or animal. In one embodiment, the disease or condition is one characterized by excessive antibody production, and in particular, excessive monoclonal antibody production. The methods of the invention utilize mass spectrometry for quantitative monitoring and detection of antibody produced by the plasma cells. The methods of the invention can be utilized for diagnosis, monitoring, and/or prognosis of multiple myeloma, monoclonal gammopathy, and other immunological or hematological conditions and disorders. In addition to detecting and quantifying antibody in a sample, other biological markers, such as serum albumin and/or beta-2-microglobulin, can also be detected and quantified using the present invention, and in combination with detection and quantification of antibody. Thus, in one embodiment, both antibody and serum albumin and/or beta-2-microglobulin are detected and quantified using mass spectrometry and a diagnosis or prognosis made based on the results and levels detected.

In one embodiment of a method of the present invention, a biological sample, such as a blood or serum sample, is treated to isolate the target protein therein. In one embodiment, the biological sample is subjected to size exclusion chromatography, gel electrophoresis, and/or affinity chromatography to isolate the target protein. In a specific embodiment, the target protein is an antibody. The target protein is then subjected to proteolytic fragmentation to create fragments of the target protein. In a specific embodiment, the target protein fragments are prepared by exposing the protein to trypsin for a sufficient period of time. Other means for fragmentation of a target protein are known in the art and can be used in the present methods. Optionally, the target protein can be denatured prior to fragmentation. In one embodiment, treatment of the target protein with urea and disulfide reduction and cysteine alkylation can be performed. Following fragmentation of the target protein into peptides, the peptides are subjected to mass spectrometry to identify and quantify the levels of the target protein. In one embodiment, following proteolytic fragmentation and prior to quantitative mass spectrometry, the peptide fragments are separated by reverse phase chromatography and/or filtering by molecular weight. Using the results from several patient samples, specific peptides were selected to monitor each type of antibody (A, D, E, G, and M), as well as kappa and lambda light chain and other diagnostic molecules like serum albumin and beta-2-microglobulin (see Table 1). In a specific embodiment, the fragmentation peptides of the target protein are ALPAPIEK (SEQ ID NO:4) and/or DSTYSLSSTLTLSK (SEQ ID NO:28). Synthetic peptides having an amino acid substitution or synthetic stable isotope-labeled peptides (e.g., comprising $^2$H, $^{13}$C, or $^{15}$N atoms in the peptide molecule) having the same sequence as the fragmentation peptides can be used as internal standards during the mass spectrometry to provide for quantitation of the specific peptide fragments. The ratio of the peptide fragment to the isotope-labeled peptide standard can be used to calculate the quantity of the target protein. In one embodiment, the peptides are specific to heavy chains of human IgG, IgA, IgM, IgD, or IgE. In another embodiment, the peptides are specific to human kappa (κ) or lambda (λ) immunoglobulin light chains. In one embodiment, the internal standard peptides can have an amino acid sequence shown in any of SEQ ID NOs: 1 to 30, or a fragment or variant thereof. In a specific embodiment, the synthetic internal standard peptide comprises the amino acid of SEQ ID NO:4 or SEQ ID NO:28, or a fragment or variant thereof. In one embodiment, the mass spectrometry methods comprise liquid chromatography coupled to multiple reaction monitoring (LC-MRM) using a triple quadrupole mass spectrometer.

The subject invention also concerns peptides of target proteins, such as immunoglobulin heavy chain, kappa light chain, lambda light chain, serum albumin, and beta-2-microglobulin, that can be used in the methods of the present invention. In one embodiment, a peptide corresponds to a proteolytic digestion fragment of a human IgG, IgA, IgM, IgD, or IgE heavy chain, or a human kappa or lambda immunoglobulin light chain. In one embodiment, a peptide of the invention comprises one or more stable heavy isotopes, such as $^2$H, $^{13}$C, or $^{15}$N. In another embodiment, a peptide of the invention comprises one or more amino acid substitutions of similar composition (such as an alanine substituted for a glycine) from that of the sequence of target protein such that the subject peptide has a "mass shift" when compared to the corresponding peptide fragment of the target protein.

In a specific embodiment, a peptide of the invention comprises an amino acid sequence shown in any of SEQ ID NOs: to 30, or a fragment or variant thereof. In an exemplified embodiment, a peptide of the invention has the amino acid sequence of SEQ ID NO:4 (for IgG heavy chain) or SEQ ID NO:28 (for kappa light chain).

Biological samples refer to a fluid or tissue composition obtained from a human or animal. Biological samples within the scope of the invention include, but are not limited to, whole blood, peripheral blood, blood plasma, bone marrow, spleen, serum, urine, tears, saliva, sputum, exhaled breath, nasal secretions, pharyngeal exudates, bronchoalveolar lavage, tracheal aspirations, interstitial fluid, lymph fluid, meningal fluid, amniotic fluid, glandular fluid, feces, perspiration, mucous, vaginal or urethral secretion, cerebrospinal fluid, and transdermal exudate. A biological sample also includes experimentally separated fractions of all of the preceding solutions or mixtures containing homogenized solid material, such as feces, tissues, and biopsy samples.

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Figure 1A:
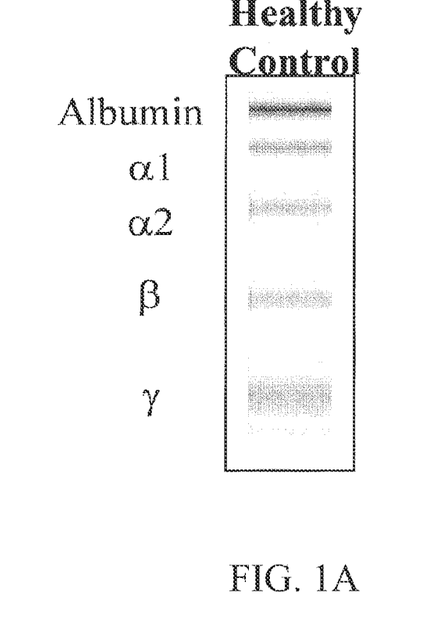
FIGS. 1A and 1B depict the antibody production for detected with conventional serum protein electrophoresis for use in multiple myeloma diagnosis and prognosis.
Figure 1B:
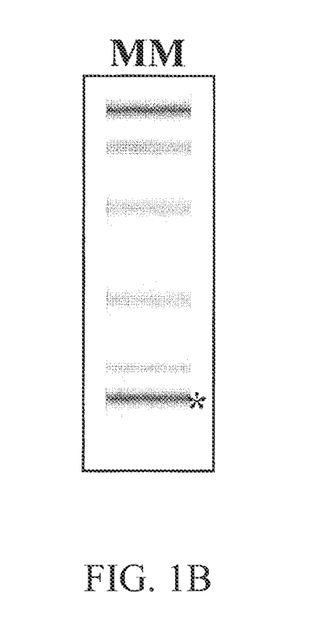
Figure 2:
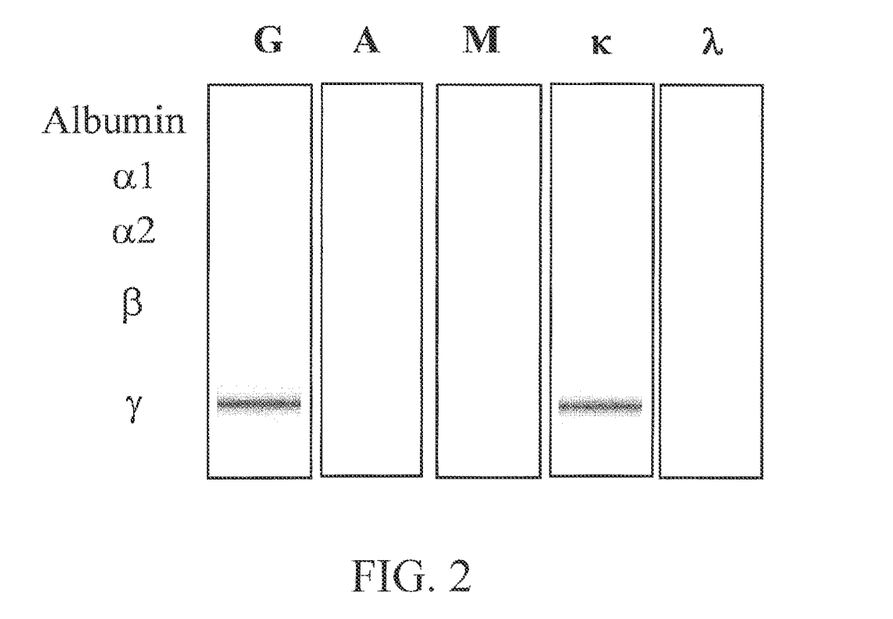
FIG. 2 depicts the antibodies identified using immunofixation electrophoresis for use in multiple myeloma diagnosis and prognosis.

In multiple myeloma, because each plasma cell secretes a unique antibody, the replication of the tumor cell and the progression of disease can be monitored by measuring the serum concentration of the monoclonal antibody it produces. Initial qualitative measurements are made using serum protein electrophoresis (SPEP) and dye visualization (see FIGS. 1A and 1B). Separation of the serum proteins is achieved, isolating albumin from four regions of globulins, termed alpha 1 (α1), alpha 2 (α2), beta (β), and gamma (γ), described by the differences in their migration relative to albumin. Normally, antibodies migrate into the γ region, but are low in intensity compared to albumin and are present only as diffuse bands (FIG. 1A). The monoclonal antibodies produced in high concentration by multiple myeloma plasma cells can be visualized as a single narrow, discrete, dark band usually in the γ region of the gel (FIG. 1B). Patients with abnormally high levels of protein in the gamma region can be diagnosed with multiple myeloma by identifying the type of monoclonal antibody using immunofixation electrophoresis (IFE), which is a separation similar to SPEP, but with specific detection for each antibody chain (FIG. 2). Typical screens test for immunoglobulin G, A, and M heavy chains, as well as kappa (κ) and lambda (λ) light chains. Immunoglobulin D or E myelomas are very rare; when suspected, lanes of the standard IFE are replaced, enabling specific detection of IgD or IgE heavy chain proteins. In the example, the patient has a tumor that produces an IgG κ monoclonal antibody protein (FIG. 2). The combination of these two tests establishes the relative amount and type of the antibody that is secreted by the multiple myeloma tumor cells. Gel-based techniques have recently been complemented by capillary array instruments that can analyze eight samples in parallel, greatly increasing the throughput and lowering the amount of sample preparation necessary (tubes of serum are simply loaded into the instrument, which automatically dilutes each sample in the buffer used for capillary electrophoresis). SPEP and IFE are performed separately.

Figure 3:
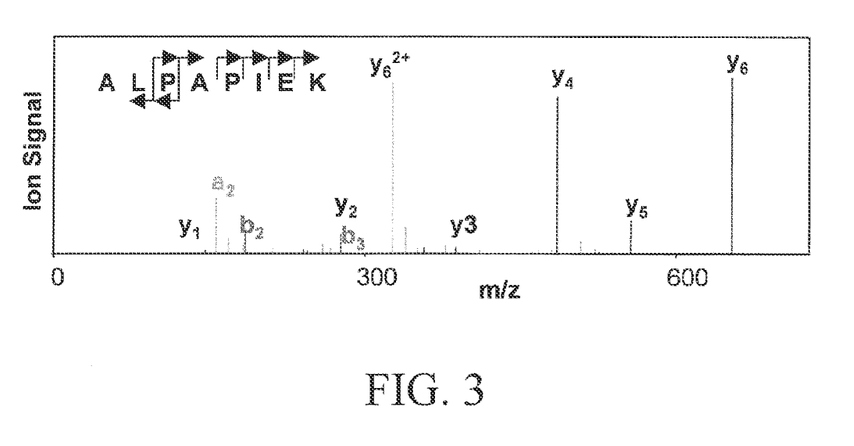
FIG. 3 depicts the multiple myeloma diagnosis and prognosis method where monoclonal spike is an IgG with κ light chain. After LC-MS/MS, peptides, such as ALPAPIEK (SEQ ID NO:4) from IgG, can be selected for quantitative mass spectrometry assays.
Figure 4:
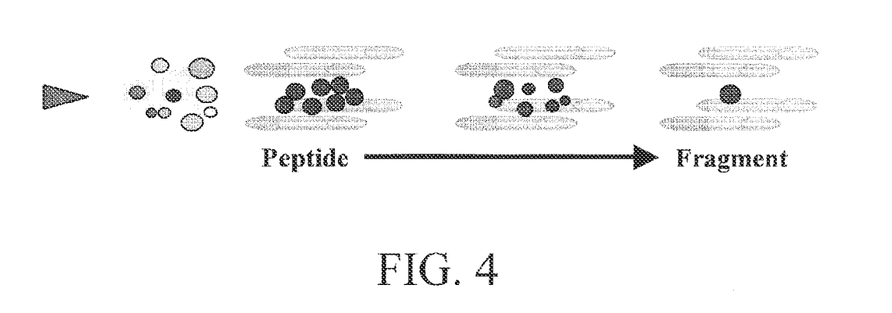
FIG. 4 depicts a schematic diagram of selected reaction monitoring used in multiple myeloma diagnosis and prognosis.

The quantitative mass spectrometry methods of the invention can replace standard art methods with a single analysis. Protein bands from SPEP have been processed for protein identification using LC-MS/MS. Constant regions on an antibody are utilized in detection for quantitative monitoring; as shown in FIG. 3, a peptide sequence ALPAPIEK (SEQ ID NO:4) is used to detect immunoglobulin G heavy chains. After generating peptides for monitoring each of the types of antibodies, a comprehensive method for antibody measurement was made. Briefly, minute volumes of serum (1 to 10 µl) were processed for detection of each of the antibody chains: G, A, M, D, E, κ, and λ. After protein denaturation with urea, disulfide reduction, and cysteine alkylation, trypsin digestion was performed. The sample was then diluted and analyzed with liquid chromatography coupled to multiple reaction monitoring (LC-MRM) on a triple quadrupole mass spectrometer (FIG. 4). Methods for quantitative mass spectrometry of other proteins, such as vitellogenin, thyroglobulin, C-reactive protein, and others, have been described in U.S. Pat. Nos. 7,544,518 and 7,163,803; Published U.S. Patent Application Nos. 2009/0011447 and 2009/0148951; and publications by Anderson and Hunter (2006) and Kuhn et al. (2004).

Figure 5:
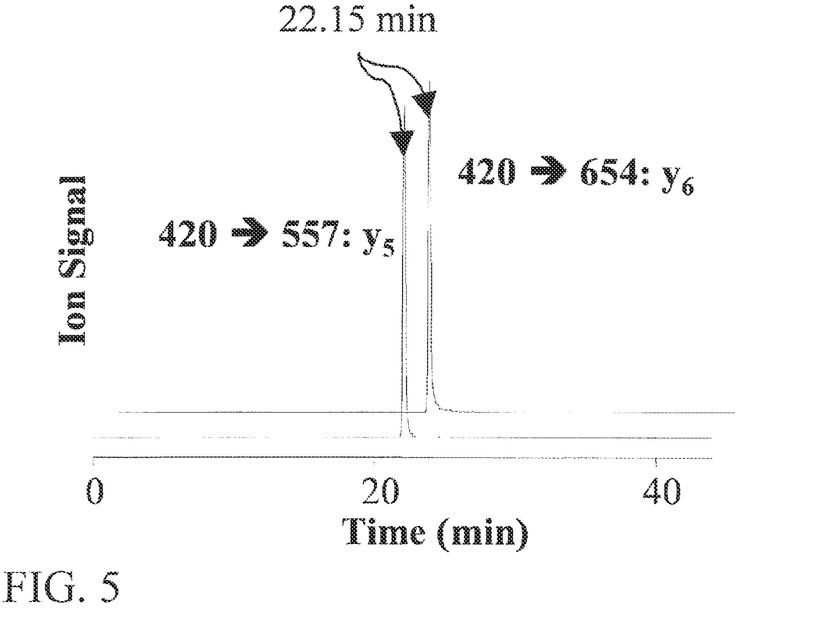
FIG. 5 depicts the abilities of multiple myeloma diagnosis and prognosis, where single molecule can be detected by filtering the m/z values for peptide and specific fragments. Using the same serum sample shown in FIG. 1B, the quantity and type of antibody are determined in a mass spectrometry assay; high levels of ALPAPIEK (SEQ ID NO:4) from IgG.
Figure 6:
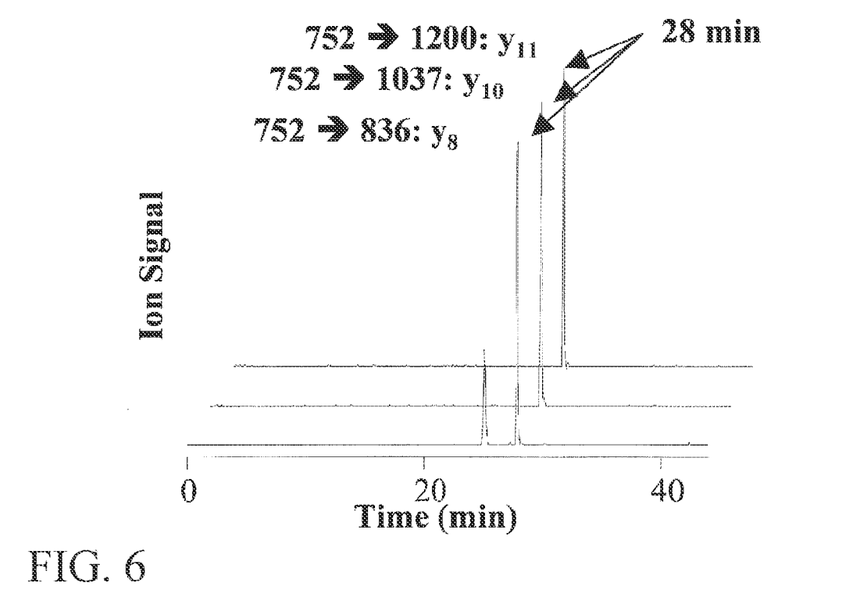
FIG. 6 depicts an assay to confirm the multiple myeloma diagnosis and prognosis method DSTYSLSSTLTLSK (SEQ ID NO:28) from κ light chain were confirmed using Multiple Reaction Monitoring.

In one embodiment, the mass spectrometer instrument selectively quantifies peptides by filtering the m/z of the intact species in the first quadrupole (Q1), fragments the molecules in the second quadrupole (Q2), and filters the m/z of a particular fragment in the third quadrupole (Q3). Each of these peptide and fragment pairs is known as a transition; the instrument measures each transition as part of a cycle, continuously moving from one to the next. For each peptide, multiple transitions are monitored; the coincidence detection of multiple fragments from the peptide increases the confidence in the assignment. Each target protein can be quantified using more than one peptide. While several rules for peptide selection have been put forward, selection of peptides in biological or clinical context frequently deviates from those guidelines. Examples of quantification with LC-MRM are shown in FIGS. 5 and 6 using the ALPAPIEK (SEQ ID NO:4) peptide from immunoglobulin G (IgG) heavy chain and DSTYSLSSTLTLSK (SEQ ID NO:28) from the κ light chain. The ion signals corresponding to the $y_5$ and $y_6$ ions of ALPAPIEK (SEQ ID NO:4) were detected at 22 minutes in FIG. 5; $y_4$ were also monitored. The $y_8$, $y_{11}$, and $y_{12}$ ion signals for DSTYSLSSTLTLSK (SEQ ID NO:28) were detected at 28 minutes, as shown in FIG. 6. These ion signals were confirmed from the sample used for the SPEP and IFE, illustrated with the diagrams in FIGS. 1 and 2.

The quantitative mass spectrometry assay of the present invention is advantageous in animal models where limited amounts of blood serum can be obtained. The implementation of a single quantitative test provides advantages over the qualitative tests currently used to follow multiple myeloma patients. The speed and parallel processing that can be achieved with automated sample handling and MS detection will also significantly improve the throughput of patient samples. The adoption of the methods of the invention at a tertiary cancer center will enable surrounding primary care physicians and hospitals to send samples to a centralized facility for processing and analysis. Point of care patient sampling can be performed with rapid turnaround of results to the treating physician (~1 day) even at a centralized facility.

TABLE 1

| Protein | Peptide Sequence | W/Z | | Transitions | | | | | |
|---|---|---|---|---|---|---|---|---|---|
| IGHA1, 2 | SAVQGPPER (SEQ ID NO: 1) | 470.747 | 4 | 498.268 | 5 | 555.289 | 6 | 683.348 | |
| IGHA1, 2 | WLQGSQELPR (SEQ ID NO: 2) | 607.320 | 6 | 729.390 | 7 | 786.411 | 8 | 914.470 | |
| | WLQGSQELPR (SEQ ID NO: 2) | 610.820 | 6 | 736.390 | 7 | 793.411 | 8 | 921.470 | |
| IGHA1 | TPLIAILSK (SEQ ID NO: 3) | 466.277 | 5 | 519.314 | 6 | 620.362 | 7 | 733.446 | |
| | TPLTAILSK (SEQ ID NO: 3) | 469.777 | 5 | 526.314 | 6 | 627.362 | 7 | 740.446 | |
| IGHA1, 3 | AEPAPIEK (SEQ ID NO: 4) | 419.756 | 4 | 486.293 | 5 | 557.330 | 6 | 654.383 | |
| IGHG1, 2 | EPQVYTLPPSR (SEQ ID NO: 5) | 643.841 | 4 | 456.257 | 6 | 670.389 | 7 | 883.452 | |
| | DPQVYTLPPSR (SEQ ID NO: 6) | 636.833 | 4 | 456.257 | 6 | 670.389 | 7 | 833.452 | |
| ICHG1 | GPSVFPLAPSSK (SEQ ID NO: 7) | 593.828 | 8 | 846.473 | 9 | 945.541 | 10 | 1032.573 | |
| | GPSVFPLAPSSK (SEQ ID NO:7) | 596.828 | 8 | 852.472 | 9 | 951.540 | 10 | 1038.573 | |
| IGHG2 | GLPAPIEK (SEQ ID NO: 8) | 412.748 | 4 | 486.293 | 5 | 557.240 | 6 | 654.383 | |
| | GLPAPIEK (SEQ ID NO: 8) | 415.748 | 4 | 492.293 | 5 | 563.330 | 6 | 660.383 | |
| IGHG3 | WYVDGVEVHNAK (SEQ ID NO: 9) | 708.850 | 6 | 697.363 | 9 | 968.480 | 11 | 1230.612 | |
| | WYVDGVEVHNAK (SEQ ID NO: 9) | 711.850 | 6 | 703.363 | 9 | 974.480 | 11 | 1236.611 | |
| IGHG3, 4 | VVSVLTVLHQDWLNGK (SEQ ID NO: 10) | 904.507 | 5 | 617.341 | 10 | 1209.638 | 11 | 1310.686 | |
| IGHG4 | SLSLSLGK (SEQ ID NO: 11) | 402.746 | 5 | 517.335 | 6 | 604.367 | 7 | 717.451 | |
| IGHM | DGFFGNPR (SEQ ID NO: 12) | 455.215 | 4 | 443.237 | 5 | 590.305 | 7 | 794.394 | |
| | DAFFGNPR (SEQ ID NO: 13) | 462.223 | 4 | 443.237 | 5 | 590.305 | 7 | 808.410 | |

TABLE 1 -continued

| Protein | Peptide Sequence | W/Z | | Transitions | | | | | |
|---|---|---|---|---|---|---|---|---|---|
| IGHM | QVGSGVTTDQVQAEAK (SEQ ID NO: 14) | 809.408 | 8 | 888.443 | 9 | 989.490 | 10 | 1090.538 | |
| IGKC | VDNALQSGNSQESVTEQDSK (SEQ ID NO: 15) | 1068.489 | 6 | 707.321 | 14 | 1495.651 | 8 | 893.421 | |
| IGKC | TVAAPSVFIFPPSDEQLK (SEQ ID NO: 16) | 973.518 | 8 | 913.463 | 9 | 1060.532 | 11 | 1320.684 | |
| | TV<u>G</u>APSVFIFPPSDEQLK (SEQ ID NO: 17) | 966.510 | 8 | 913.463 | 9 | 1060.532 | 11 | 1320.684 | |
| LAC | AAPSVTLFPPSSEELQANK (SEQ ID NO: 18) | 993.513 | 10 | 1102.538 | 11 | 119.591 | 12 | 1346.659 | |
| LAC | AGVETTTPSK (SEQ ID NO: 19) | 495.759 | 5 | 533.294 | 6 | 634.341 | 7 | 763.384 | |
| | AGVETTTPSK (SEQ ID NO: 19) | 498.759 | 5 | 539.294 | 6 | 640.341 | 7 | 769.384 | |
| IGHE | GSGFFVESR (SEQ ID NO: 20) | 502.254 | 5 | 655.357 | 6 | 802.425 | 7 | 859.447 | |
| | GS<u>A</u>FFVESR (SEQ ID NO: 21) | 509.262 | 5 | 655.357 | 6 | 802.425 | 7 | 873.462 | |
| IGHD | EPAAQAPVK (SEQ ID NO: 22) | 455.754 | 5 | 542.330 | 6 | 613.367 | 7 | 684.404 | |
| | EPA<u>G</u>QAPVK (SEQ ID NO: 23) | 448.746 | 5 | 542.330 | 6 | 599.351 | 7 | 670.388 | |
| IGHD | VRPGGVEEGLLER (SEQ ID NO: 24) | 678.362 | 7 | 845.437 | 10 | 1058.548 | 11 | 1159.596 | |
| ALBU | LVNEVTEFAK (SEQ ID NO: 25) | 575.312 | 6 | 694.378 | 7 | 823.420 | 8 | 937.463 | |
| | LVN<u>D</u>VTEFAK (SEQ ID NO: 26) | 568.303 | 6 | 694.378 | 7 | 809.404 | 8 | 923.447 | |
| ALBU | AEFAEVSK (SEQ ID NO: 27) | 440.725 | 5 | 533.294 | 6 | 680.362 | 7 | 809.404 | |

Table 1 displays a list of monitored peptides of interest and their corresponding internal standards (where applicable) along with the Y-ion transitions used in MRM. The underlining designates an amino acid that can be labeled with a stable heavy isotope.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 7,544,518
U.S. Pat. No. 7,163,803
U.S. Published Patent Application No. 2009/0011447
U.S. Published Patent Application No. 2009/0148951
Anderson, L and Hunter, C (2006) "Quantitative mass spectrometric multiple reaction monitoring assays for major plasma proteins" *Mole. Cell. Proteomics*, 5:573-588.
Chanan-Khan, A A and Lee, K (2007) "Pegylated liposomal doxorubicin and immunomodulatory drug combinations in multiple myeloma: rationale and clinical experience" *Clin. Lymph. Myel.*, 7:S163-S169.
Chauhan, D et al. (1997) "Interleukin-6 inhibits Fas-induced apoptosis and stress-activated protein kinase activation in multiple myeloma cells" *Blood*, 89:227-234.
Chen, Q et al. (2005) "The FA/BRCA pathway is involved in Melphalan-induced DNA interstrand cross-link repair and accounts for Melphalan resistance in multiple myeloma cells" *Blood*, 106:698-705.
Dalton, W S (2003) "The tumor microenvironment: focus on myeloma" *Cancer Treat Rev.*, 29 (Suppl 1):11-19.
Damiano, J S et al. (1999) "Cell adhesion mediated drug resistance (CAM-DR): role of integrins and resistance to apoptosis in human myeloma cell lines" *Blood*, 93:1658-1667.
Durie, B G and Salmon, S E (1975) "A clinical staging system for multiple myeloma. Correlation of measured myeloma cell mass with presenting clinical features, response to treatment, and survival" *Cancer*, 36:842-854.
Falco, P et al. (2007) "Melphalan and its role in the management of patients with multiple myeloma" *Expert. Rev. Anticancer Ther.* 7:945-957.
Fonseca, R and Stewart, A K (2007) "Targeted therapeutics for multiple myeloma: the arrival of a risk-stratified approach" *Mol. Cancer Ther.*, 6:802-810.
Greipp, P R et al. (2005) "International staging system for multiple myeloma" *J. Clin. Oncol.* 23:3412-3420.
Hazlehurst, L A et al. (2003) "Role of the tumor microenvironment in mediating de novo resistance to drugs and physiological mediators of cell death" *Oncogene*, 22:7396-7402.
Kyle, R A et al (2006) "Prevalence of monoclonal gammopathy of undetermined significance" *N. Engl. J. Med.*, 354:1362-1369.
Kuhn, E. et al. (2004) "Quantification of C-reactive protein in the serum of patients with rheumatoid arthritis using multiple reaction monitoring mass spectrometry and $^{13}$C-labeled peptide standards" *Proteomics*, 4:1175-1186.

Li, Z W and Dalton, W S (2006) "Tumor microenvironment and drug resistance in hematologic malignancies" *Blood Rev.*, 20 (6):333-342.

Ma, M H et al. (2003) "The proteasome inhibitor PS-341 markedly enhances sensitivity of multiple myeloma tumor cells to chemotherapeutic agents" *Clin, Cancer Res.*, 9:1136-1144.

Manochakian, R et al. (2007) "Clinical Impact of Bortezomib in frontline regimens for patients with multiple myeloma" *The Oncologist*, 12:978-990.

Meister, S et al. (2007) "Extensive immunoglobulin production sensitizes myeloma cells for proteasome inhibition" *Cancer Res.*, 67:1783-1792.

Merchionne, F et al. (2007) "New therapies in multiple myeloma" *Clin. Exp. Med.* 7:83-97.

Richardson, P G et al. (2007) "The emerging role of novel therapies for the treatment of relapsed myeloma" *J. Natl. Comp. Cancer Network*, 5:149-162.

Singhal, S and Mehta, J (2007) "Lenalidomide in myeloma" *Curr. Treatment Options in Oncology*, 8:154-163.

Srikanth, M, Davies, F E, Morgan, G J (2008) "An update on drug combinations for treatment of myeloma" *Expert Opn. Investig. Drugs*, 17:1-12.

Thomas, S and Alexanian, R (2007) "Current treatment strategies for multiple myeloma" *Clin. Lymph Myel.*, 7:S139-S144.

Urashima, M et al. (1997) "Interleukin-6 overcomes p21WAF1 upregulation and G1 growth arrest induced by dexamethasone and interferon-gamma in multiple myeloma cells" *Blood*, 90:279-289.

Voorhees, P M and Orlowski, R Z (2007) "Emerging data on the use of anthracyclines in combination with Bortezomib in multiple myeloma" *Clin. Lymph. Myel.* 7:S156-S162.

We claim:

1. A method for diagnosing, monitoring the progress of, and/or providing a prognosis of multiple myeloma (MM) or monoclonal gammopathy of undetermined significance (MGUS) in a person or animal, said method comprising
   (a) isolating immunoglobulin proteins from a biological sample from the person or animal;
   (b) fragmenting the immunoglobulin proteins to create peptide fragments thereof;
   (c) subjecting the peptide fragments of the immunoglobulin proteins to quantitative mass spectrometry to simultaneously quantify the amount of IgG, IgA, IgM, IgD, and IgE heavy chains, and optionally the amount of kappa light chains and lambda light chains, in the biological sample; and
   (d) using the quantity of IgG, IgA, IgM, IgD, and IgE heavy chains, and optionally the amount of kappa light chains and lambda light chains, in the biological sample to diagnose, monitor the progress of, and/or provide the prognosis of the MM or MGUS in the person or animal.

2. The method according to claim 1, wherein the IgG, IgA, IgM, IgD, and IgE heavy chains, and optionally the kappa light chains and lambda light chains, are quantified by spiking in a known amount of a specific labeled peptide corresponding to a fragment of IgG, IgA, IgM, IgD, or IgE heavy chain, kappa light chain, or lambda light chain during mass spectrometry, wherein the specific labeled peptide comprises a heavy isotope label or has an amino acid substitution to create a mass difference between the peptide fragment and the specific labeled peptide.

3. The method according to claim 2, wherein the heavy isotope label is $^2$H, $^{13}$C, or $^{15}$N.

4. The method according to claim 2, wherein the specific labeled peptide comprises an amino acid sequence of any of SEQ ID NO:1 to SEQ ID NO:30.

5. The method according to claim 2, wherein the specific labeled peptide corresponds to a fragment of a human antibody heavy chain of IgG and comprises the amino acid sequence ALPAPIEK (SEQ ID NO:4).

6. The method according to claim 2, wherein the specific labeled peptide corresponds to a fragment of a human antibody kappa light chain and comprises the amino acid sequence DSTYSLSSTL TLSK (SEQ ID NO:28).

7. The method according to claim 1, wherein the immunoglobulin proteins are denatured prior to fragmentation.

8. The method according to claim 7, wherein the immunoglobulin proteins are denatured by treatment with urea, disulfide reduction, and/or cysteine alkylation.

9. The method according to claim 1, wherein the immunoglobulin proteins are fragmented by proteolytic enzyme digestion.

10. The method according to claim 9, wherein the proteolytic enzyme is trypsin.

11. The method according to claim 1, wherein the immunoglobulin proteins are isolated by size exclusion chromatography, gel electrophoresis, affinity chromatography, or a combination thereof.

12. The method according to claim 1, wherein the quantitative mass spectrometry comprises liquid chromatography coupled to multiple reaction monitoring (LC-VIRM).

13. The method according to claim 12, wherein the quantitative mass spectrometry is conducted on a triple quadrupole mass spectrometer.

14. The method according to claim 2, wherein the amino acid substitution comprises substitution of alanine for glycine.

15. The method according to claim 1, wherein the method is used to monitor for progression of monoclonal gammopathy of undetermined significance in the person or animal to multiple myeloma.

16. The method according to claim 1, wherein the method is used to monitor the efficacy of a treatment regimen on a person or animal with multiple myeloma or MGUS.

17. The method according to claim 1, further comprising treating the subject for MM or MGUS if the identity and quantity of the immunoglobulin proteins in the biological sample indicates elevated levels of total immunoglobulin in the person or animal.

* * * * *

SEQUENCE LISTING

```
<160> NUMBER OF SEQ ID NOS: 30

<210> SEQ ID NO 1
<211> LENGTH: 9
<212> TYPE: PRT
<213> ORGANISM: Homo sapiens

<400> SEQUENCE: 1

Ser Ala Val Gln Gly Pro Pro Glu Arg
1               5

<210> SEQ ID NO 2
<211> LENGTH: 10
<212> TYPE: PRT
<213> ORGANISM: Homo sapiens

<400> SEQUENCE: 2

Trp Leu Gln Gly Ser Gln Glu Leu Pro Arg
1               5                   10

<210> SEQ ID NO 3
<211> LENGTH: 9
<212> TYPE: PRT
<213> ORGANISM: Homo sapiens

<400> SEQUENCE: 3

Thr Pro Leu Thr Ala Thr Leu Ser Lys
1               5

<210> SEQ ID NO 4
<211> LENGTH: 8
<212> TYPE: PRT
<213> ORGANISM: Homo sapiens

<400> SEQUENCE: 4

Ala Leu Pro Ala Pro Ile Glu Lys
1               5

<210> SEQ ID NO 5
<211> LENGTH: 11
<212> TYPE: PRT
<213> ORGANISM: Homo sapiens

<400> SEQUENCE: 5

Glu Pro Gln Val Tyr Thr Leu Pro Pro Ser Arg
1               5                   10
```

```
<210> SEQ ID NO 6
<211> LENGTH: 11
<212> TYPE: PRT
<213> ORGANISM: Homo sapiens

<400> SEQUENCE: 6

Asp Pro Gln Val Tyr Thr Leu Pro Pro Ser Arg
1               5                   10

<210> SEQ ID NO 7
<211> LENGTH: 12
<212> TYPE: PRT
<213> ORGANISM: Homo sapiens

<400> SEQUENCE: 7

Gly Pro Ser Val Phe Pro Leu Ala Pro Ser Ser Lys
1               5                   10

<210> SEQ ID NO 8
<211> LENGTH: 8
<212> TYPE: PRT
<213> ORGANISM: Homo sapiens

<400> SEQUENCE: 8

Gly Leu Pro Ala Pro Ile Glu Lys
1               5

<210> SEQ ID NO 9
<211> LENGTH: 12
<212> TYPE: PRT
<213> ORGANISM: Homo sapiens

<400> SEQUENCE: 9

Trp Tyr Val Asp Gly Val Glu Val His Asn Ala Lys
1               5                   10

<210> SEQ ID NO 10
<211> LENGTH: 16
<212> TYPE: PRT
<213> ORGANISM: Homo sapiens

<400> SEQUENCE: 10

Val Val Ser Val Leu Thr Val Leu His Gln Asp Trp Leu Asn Gly Lys
1               5                   10                  15

<210> SEQ ID NO 11
<211> LENGTH: 8
<212> TYPE: PRT
<213> ORGANISM: Homo sapiens

<400> SEQUENCE: 11

Ser Leu Ser Leu Ser Leu Gly Lys
1               5

<210> SEQ ID NO 12
<211> LENGTH: 8
<212> TYPE: PRT
<213> ORGANISM: Homo sapiens

<400> SEQUENCE: 12

Asp Gly Phe Phe Gly Asn Pro Arg
1               5
```

```
<210> SEQ ID NO 13
<211> LENGTH: 8
<212> TYPE: PRT
<213> ORGANISM: Homo sapiens

<400> SEQUENCE: 13

Asp Ala Phe Phe Gly Asn Pro Arg
1               5

<210> SEQ ID NO 14
<211> LENGTH: 16
<212> TYPE: PRT
<213> ORGANISM: Homo sapiens

<400> SEQUENCE: 14

Gln Val Gly Ser Gly Val Thr Thr Asp Gln Val Gln Ala Glu Ala Lys
1               5                   10                  15

<210> SEQ ID NO 15
<211> LENGTH: 20
<212> TYPE: PRT
<213> ORGANISM: Homo sapiens

<400> SEQUENCE: 15

Val Asp Asn Ala Leu Gln Ser Gly Asn Ser Gln Glu Ser Val Thr Glu
1               5                   10                  15

Gln Asp Ser Lys
            20

<210> SEQ ID NO 16
<211> LENGTH: 18
<212> TYPE: PRT
<213> ORGANISM: Homo sapiens

<400> SEQUENCE: 16

Thr Val Ala Ala Pro Ser Val Phe Ile Phe Pro Pro Ser Asp Glu Gln
1               5                   10                  15

Leu Lys

<210> SEQ ID NO 17
<211> LENGTH: 18
<212> TYPE: PRT
<213> ORGANISM: Homo sapiens

<400> SEQUENCE: 17

Thr Val Gly Ala Pro Ser Val Phe Ile Phe Pro Pro Ser Asp Glu Gln
1               5                   10                  15

Leu Lys

<210> SEQ ID NO 18
<211> LENGTH: 19
<212> TYPE: PRT
<213> ORGANISM: Homo sapiens

<400> SEQUENCE: 18

Ala Ala Pro Ser Val Thr Leu Phe Pro Pro Ser Ser Glu Glu Leu Gln
1               5                   10                  15

Ala Asn Lys

<210> SEQ ID NO 19
<211> LENGTH: 10
<212> TYPE: PRT
<213> ORGANISM: Homo sapiens
```

```
<400> SEQUENCE: 19

Ala Gly Val Glu Thr Thr Pro Ser Lys
1               5                   10

<210> SEQ ID NO 20
<211> LENGTH: 9
<212> TYPE: PRT
<213> ORGANISM: Homo sapiens

<400> SEQUENCE: 20

Gly Ser Gly Phe Phe Val Phe Ser Arg
1               5

<210> SEQ ID NO 21
<211> LENGTH: 9
<212> TYPE: PRT
<213> ORGANISM: Homo sapiens

<400> SEQUENCE: 21

Gly Ser Ala Phe Phe Val Phe Ser Arg
1               5

<210> SEQ ID NO 22
<211> LENGTH: 9
<212> TYPE: PRT
<213> ORGANISM: Homo sapiens

<400> SEQUENCE: 22

Glu Pro Ala Ala Gln Ala Pro Val Lys
1               5

<210> SEQ ID NO 23
<211> LENGTH: 9
<212> TYPE: PRT
<213> ORGANISM: Homo sapiens

<400> SEQUENCE: 23

Glu Pro Ala Gly Gln Ala Pro Val Lys
1               5

<210> SEQ ID NO 24
<211> LENGTH: 13
<212> TYPE: PRT
<213> ORGANISM: Homo sapiens

<400> SEQUENCE: 24

Val Arg Pro Gly Gly Val Glu Glu Gly Leu Leu Glu Arg
1               5                   10

<210> SEQ ID NO 25
<211> LENGTH: 10
<212> TYPE: PRT
<213> ORGANISM: Homo sapiens

<400> SEQUENCE: 25

Leu Val Asn Glu Val Thr Glu Phe Ala Lys
1               5                   10

<210> SEQ ID NO 26
<211> LENGTH: 10
<212> TYPE: PRT
<213> ORGANISM: Homo sapiens
```

```
<400> SEQUENCE: 26

Leu Val Asn Asp Val Thr Glu Phe Ala Lys
1               5                   10

<210> SEQ ID NO 27
<211> LENGTH: 8
<212> TYPE: PRT
<213> ORGANISM: Homo sapiens

<400> SEQUENCE: 27

Ala Glu Phe Ala Glu Val Ser Lys
1               5

<210> SEQ ID NO 28
<211> LENGTH: 14
<212> TYPE: PRT
<213> ORGANISM: Homo sapiens

<400> SEQUENCE: 28

Asp Ser Thr Tyr Ser Leu Ser Ser Thr Leu Thr Leu Ser Lys
1               5                   10

<210> SEQ ID NO 29
<211> LENGTH: 15
<212> TYPE: PRT
<213> ORGANISM: Homo sapiens

<400> SEQUENCE: 29

Val Phe Ala Ile Pro Pro Ser Phe Ala Ser Ile Phe Leu Thr Lys
1               5                   10                  15

<210> SEQ ID NO 30
<211> LENGTH: 14
<212> TYPE: PRT
<213> ORGANISM: Homo sapiens

<400> SEQUENCE: 30

Asp Ala Ser Gly Val Thr Phe Thr Trp Thr Pro Ser Ser Lys
1               5                   10
```